US011928891B2

(12) United States Patent
de Paula et al.

(10) Patent No.: US 11,928,891 B2
(45) Date of Patent: Mar. 12, 2024

(54) ADAPTING PHYSICAL ACTIVITIES AND EXERCISES BASED ON FACIAL ANALYSIS BY IMAGE PROCESSING

(71) Applicant: INTERNATIONAL BUSINESS MACHINES CORPORATION, Armonk, NY (US)

(72) Inventors: Rogerio Abreu de Paula, Sao Paulo (BR); Juliana de Melo Batista dos Santos, Sao Paulo (BR); Andrea Britto Mattos Lima, Sao Paulo (BR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 705 days.

(21) Appl. No.: 16/677,832

(22) Filed: Nov. 8, 2019

(65) Prior Publication Data
US 2020/0074155 A1 Mar. 5, 2020

Related U.S. Application Data

(63) Continuation of application No. 15/248,549, filed on Aug. 26, 2016, now Pat. No. 10,628,663.

(51) Int. Cl.
*G06V 40/16* (2022.01)
*A61B 5/00* (2006.01)
(Continued)

(52) U.S. Cl.
CPC .......... *G06V 40/174* (2022.01); *A61B 5/0077* (2013.01); *A61B 5/0816* (2013.01);
(Continued)

(58) Field of Classification Search
CPC .. G06V 40/174; A61B 5/0077; A61B 5/0816; A61B 5/1176; A61B 5/165;
(Continued)

(56) References Cited

U.S. PATENT DOCUMENTS

| 5,645,513 A | 7/1997 | Haydocy et al. |
| 5,706,822 A | 1/1998 | Khavari |
| (Continued) | | |

FOREIGN PATENT DOCUMENTS

| DE | 2822343 | 11/1979 |
| EP | 2676212 | 12/2013 |
| WO | 2008157622 | 12/2008 |

OTHER PUBLICATIONS

P. Werner, A. Al-Hamadi, R. Niese, S. Walter, S. Gruss and H. C. Traue, "Automatic Pain Recognition from Video and Biomedical Signals," 2014 22nd International Conference on Pattern Recognition, 2014, pp. 4582-4587, doi: 10.1109/ICPR.2014.784. 2014.*

(Continued)

*Primary Examiner* — Sumati Lefkowitz
*Assistant Examiner* — Elisa M Rice
(74) *Attorney, Agent, or Firm* — Michael A. Petrocelli; Andrew D. Wright; Calderon Safran & Cole, P.C.

(57) ABSTRACT

Systems and methods for adapting physical activities and exercises based on facial analysis by image processing are disclosed. A method includes: identifying, by a computer device, a user; receiving, by the computer device, video data of a face region of the user while the user is engaged in exercise or physical activity; analyzing, by the computer device, the video data to determine a detected state of the user, wherein the analyzing the video data includes performing facial analysis using the video data; and providing, by the computer device, feedback to the user based on the analyzing the video data.

20 Claims, 3 Drawing Sheets

(51) Int. Cl.
  *A61B 5/08* (2006.01)
  *A61B 5/113* (2006.01)
  *A61B 5/1171* (2016.01)
  *A61B 5/16* (2006.01)
(52) U.S. Cl.
  CPC ............ *A61B 5/1176* (2013.01); *A61B 5/165* (2013.01); *A61B 5/4266* (2013.01); *A61B 5/113* (2013.01)
(58) Field of Classification Search
  CPC ..... A61B 5/4266; A61B 5/113; A61B 5/4824; A61B 5/0013; A61B 5/486; A61B 2576/00; G06K 9/00302; A61M 2021/0066
  See application file for complete search history.

(56) References Cited

U.S. PATENT DOCUMENTS

| | | | |
|---|---|---|---|
| 5,785,666 A * | 7/1998 | Costello | A61B 5/486 600/595 |
| 5,921,891 A | 7/1999 | Browne | |
| 6,132,337 A | 10/2000 | Krupka et al. | |
| 7,192,401 B2 | 3/2007 | Saalasti et al. | |
| 7,388,971 B2 | 6/2008 | Rice et al. | |
| 7,805,186 B2 | 9/2010 | Pulkkinen et al. | |
| 8,206,269 B2 | 6/2012 | Fabbri et al. | |
| 8,620,146 B1 | 12/2013 | Coleman | |
| 8,795,138 B1 | 8/2014 | Yeh et al. | |
| 9,154,739 B1 | 10/2015 | Nicolaou et al. | |
| 9,785,827 B1 | 10/2017 | Ray | |
| 2003/0149344 A1 | 8/2003 | Nizan | |
| 2005/0187437 A1 | 8/2005 | Matsugu et al. | |
| 2006/0153430 A1 | 7/2006 | Canzler et al. | |
| 2006/0190419 A1 | 8/2006 | Bunn et al. | |
| 2008/0119763 A1 | 5/2008 | Wiener | |
| 2009/0221338 A1 | 9/2009 | Stewart et al. | |
| 2011/0008761 A1 | 1/2011 | Hakopian et al. | |
| 2011/0181684 A1 | 7/2011 | Salamatov et al. | |
| 2012/0212505 A1 | 8/2012 | Burroughs et al. | |
| 2012/0296455 A1 | 11/2012 | Ohnemus et al. | |
| 2013/0171599 A1 | 7/2013 | Bleich et al. | |
| 2013/0252216 A1 | 9/2013 | Clavin et al. | |
| 2014/0016860 A1 | 1/2014 | Senechal et al. | |
| 2014/0081661 A1 | 3/2014 | Fu et al. | |
| 2014/0161421 A1 * | 6/2014 | Shoemaker | G06T 7/0016 386/278 |
| 2014/0244008 A1 | 8/2014 | Kennett et al. | |
| 2015/0025335 A1 | 1/2015 | Jain et al. | |
| 2015/0079563 A1 | 3/2015 | Yeh et al. | |
| 2015/0139502 A1 | 5/2015 | Holohan | |
| 2015/0196805 A1 | 7/2015 | Koduri et al. | |
| 2016/0066835 A1 * | 3/2016 | He | A63B 24/0087 482/4 |
| 2018/0103913 A1 * | 4/2018 | Tzvieli | A61B 5/165 |

OTHER PUBLICATIONS

Agrawal et al., "Mood Detection: Implementing a facial expression recognition system", CS 229 Machine Learning Final Projects, 2009, 5 pages.

Florea et al., "Pain Intensity Estimation by a Self{Taught Selection of Histograms of Topographical Features", Mar. 26, 2015, 19 pages.

Kulkarni et al., "Facial expression (mood) recognition from facial images using committee neural networks", BioMedical Engineering Online, Aug. 5, 2009, 12 pages.

Calistra, "60 Facial Recognition Databases (/blog/60-facial recognitiondatabases)", https://www.kairos.com/blog/60-facial-recognition-databases, Kairos Human Analytics Biogs, May 7, 2015, 25 pages.

List of IBM Patents or Patent Applications Treated as Related, dated Nov. 5, 2019, 1 page.

Notice of Allowance dated Dec. 4, 2019 in related U.S. Appl. No. 15/248,549, 11 pages.

* cited by examiner

ADAPTING PHYSICAL ACTIVITIES AND EXERCISES BASED ON FACIAL ANALYSIS BY IMAGE PROCESSING

BACKGROUND

The present invention generally relates to monitoring and analyzing physical activities such as exercise and, more particularly, to a system and method for adapting physical activities and exercises based on facial analysis by image processing.

Exercise and physical activities have been demonstrated as being useful for a person to maintain healthy habits, decrease the risk of certain diseases, avoid injuries, and help to feel better physically and mentally. However, exercising and performing physical activities without proper orientation can have the opposite effect, being occasionally harmful to the person.

While a person is exercising, it is not trivial to assess whether the effort level employed by the person is commensurate with what has been prescribed by a professional (e.g., a medical professional or trainer who prescribes certain exercise) and/or is within health limits of the person. This is because the effort level employed by the person may be based on a combination of plural variables that may be manifested in different physiological parameters. Thus, sometimes, not even the person who is exercising is able of measuring their true effort level, and this may result in an inefficient exercise or may even cause injuries.

SUMMARY

In a first aspect of the invention, there is a method that includes: identifying, by a computer device, a user; receiving, by the computer device, video data of a face region of the user while the user is engaged in exercise or physical activity; analyzing, by the computer device, the video data to determine a detected state of the user, wherein the analyzing the video data comprises performing facial analysis using the video data; and providing, by the computer device, feedback to the user based on the analyzing the video data.

In another aspect of the invention, there is a system that includes: a CPU, a computer readable memory and a computer readable storage medium associated with a computing device; program instructions to receive video data of a face region of the user while the user is engaged in exercise or physical activity; program instructions to analyze the video data using facial analysis to determine a detected state of the user; and program instructions to provide feedback to the user based on comparing the detected state to a prescribed training rule. The program instructions are stored on the computer readable storage medium for execution by the CPU via the computer readable memory.

In another aspect of the invention, there is a computer program product that includes a computer readable storage medium having program instructions embodied therewith. The program instructions are executable by a computing device to cause the computing device to: receive video data of a face region of the user while the user is engaged in exercise or physical activity; analyze the video data using facial analysis to determine a state of the user based on facial data of the user; and provide feedback to the user based on the analyzing the video

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

Figure 1:
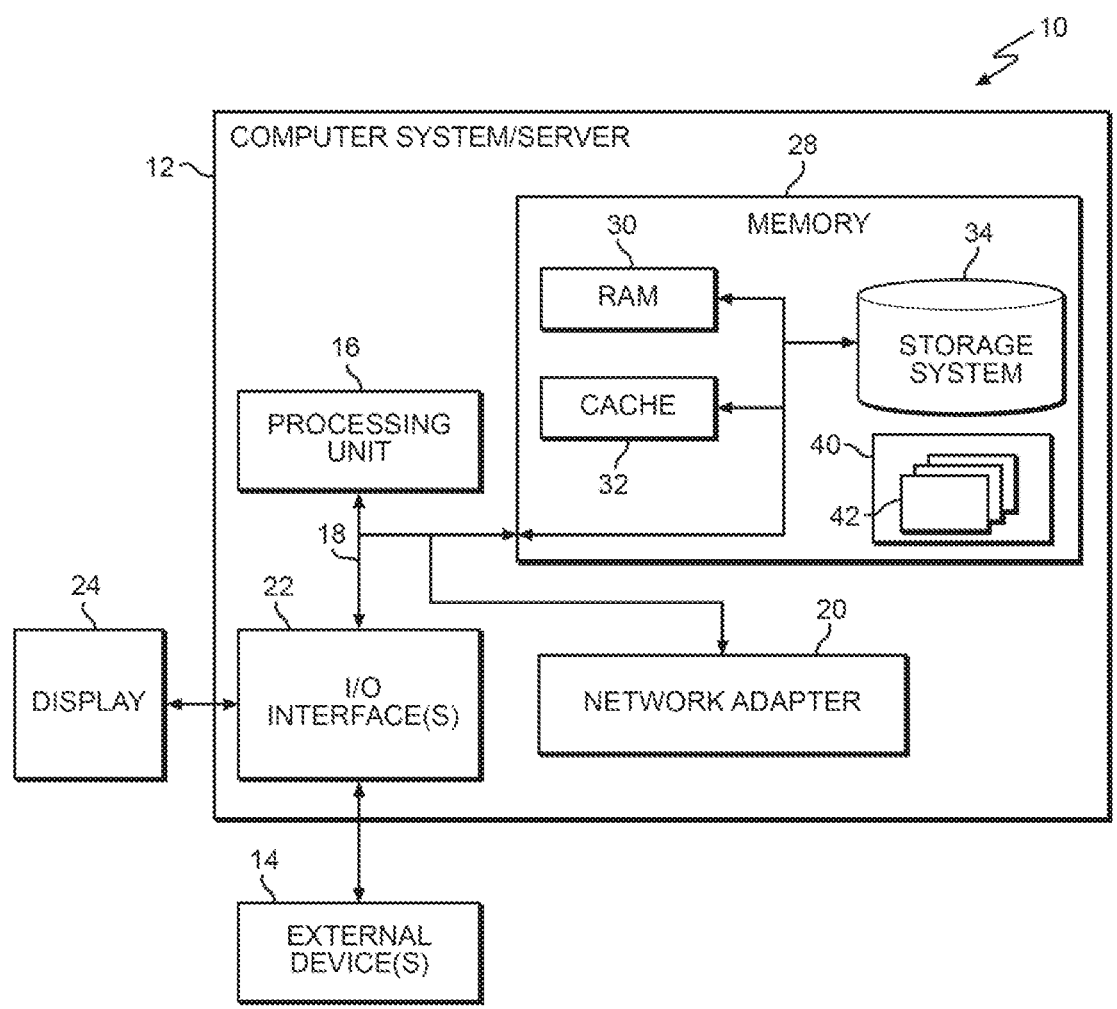
FIG. 1 depicts a computing infrastructure according to an embodiment of the present invention.

The present invention generally relates to monitoring and analyzing physical activities such as exercise and, more particularly, to a system and method for adapting physical activities and exercises based on facial analysis by image processing. According to aspects of the invention, image processing is used to provide real-time feedback to a user when the user is performing physical activities such as exercising. In embodiments, video data of a face region of the user is obtained while the user is exercising, and real time feedback is provided to the user based on analyzing the video data. The analysis of the video data may include determining a detected state of the user and comparing the detected state to a user data. The detected state may include at least one from the group consisting of: facial expression (e.g., tired, bored, calm, level of exertion, level of pain); perspiration detection; breathing interval estimation; and skin tone change. The feedback may include at least one from the group consisting of: displaying an indication of the detected state; displaying an indication of the user data; displaying a recommendation; and automatically adjusting an element of the user's environment. In this manner, implementations of the invention provide a user with real time feedback about their exercising so that the user may make an informed decision about how to continue or modify the exercising.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring now to FIG. 1, a schematic of an example of a computing infrastructure is shown. Computing infrastructure 10 is only one example of a suitable computing infrastructure and is not intended to suggest any limitation as to the scope of use or functionality of embodiments of the invention described herein. Regardless, computing infrastructure 10 is capable of being implemented and/or performing any of the functionality set forth hereinabove.

In computing infrastructure 10 there is a computer system (or server) 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system 12 in computing infrastructure 10 is shown in the form of a general-purpose computing device. The components of computer system 12 may include, but are not limited to, one or more processors or processing units (e.g., CPU) 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Figure 2:
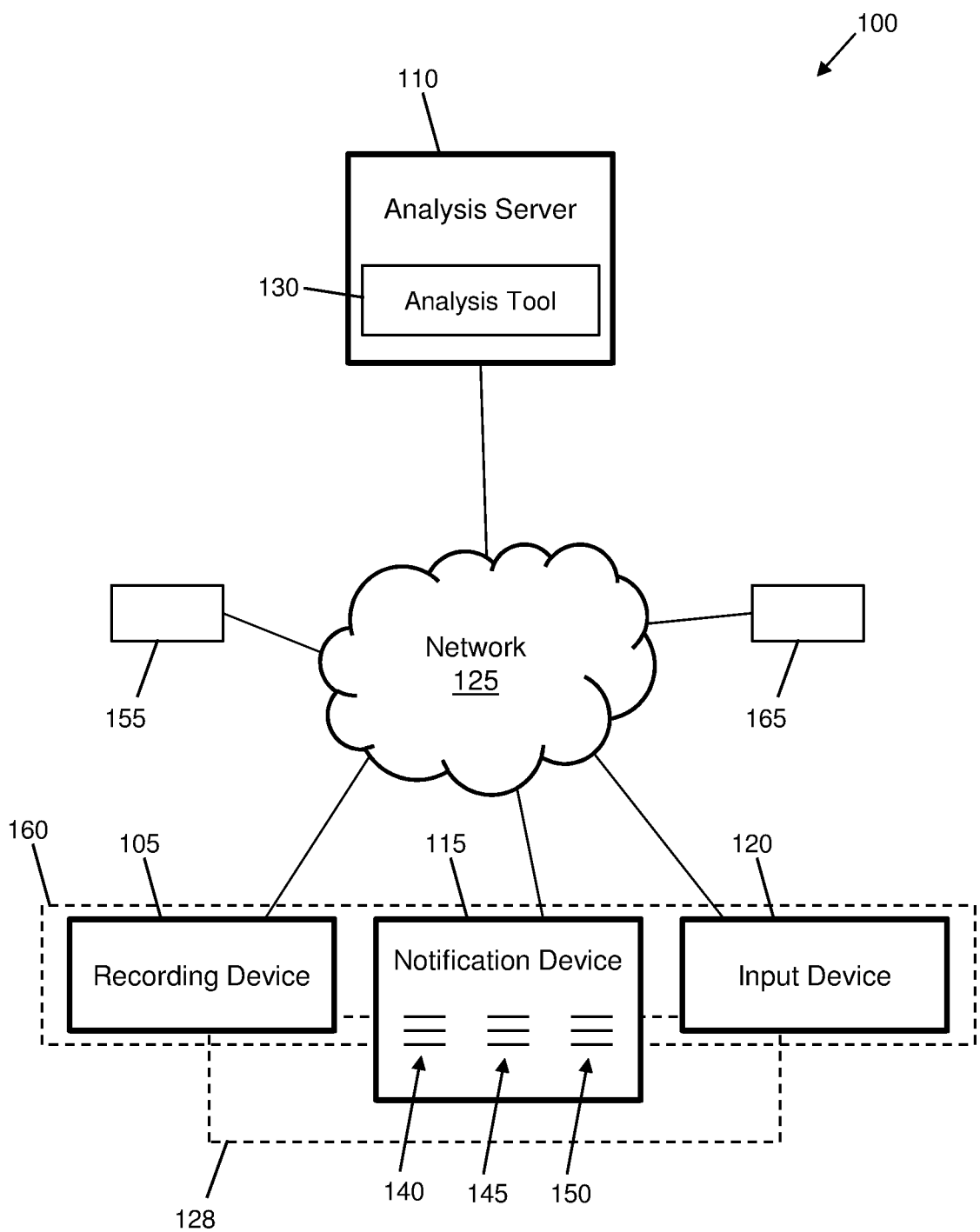
FIG. 2 shows a block diagram of an exemplary system in accordance with aspects of the invention.

FIG. 2 shows a block diagram of an exemplary system 100 in accordance with aspects of the invention. In embodiments, the system 100 includes a recording device 105, an analysis server 110, a notification device 115, and an input device 120. The devices 105, 110, 115, 120 of the system 100 may be operatively connected to a communication network 125 that supports computer-based communication between computer devices. The network 125 may be any desired network or combination of networks, including but not limited to: LAN, WAN, and the Internet. The devices of the system 100 may communicate with one another using, for example, application programming interface (API) calls or other suitable methods of communication.

According to aspects of the invention, the recording device 105 comprises a video camera that is configured to capture video data of a face region of a user that is exercising or performing other physical activity. The recording device 105 may be physically attached to equipment 128 (e.g., a treadmill, stationary bicycle, rowing machine, weight machine, etc.) on which the user is exercising, such that the field of view of the recording device 105 includes a face region of the user exercising on the equipment. Alternatively, the recording device 105 may be attached to a ceiling, wall, floor or other structure that provides the recording device 105 a field of view that includes a face region of the user who is exercising. Alternatively, the recording device 105 may be attached to moveable object, such as an unmanned aerial vehicle, that provides the recording device 105 a field of view that includes a face region of the user who is exercising. The recording device 105 may comprise any suitable type of device that includes a video camera, such as a stand-alone camera, a smartphone, or an unmanned aerial vehicle onboard camera. In embodiments, the recording device 105 transmits the video data to the analysis server 110 via the network 125.

According to aspects of the invention, the analysis server 110 runs an analysis tool 130. The analysis server 110 may be a computer system 12 and the analysis tool 130 may be a program module 42 described with respect to FIG. 1. In embodiments, the analysis server 110 running the analysis tool 130 may perform one or more of the functions described herein, including: receive video data from the recording device 105; analyze the video data to determine a detected state of the user; compare the detected state to user data; and provide feedback to the user based on the comparison of the detected state to the user data.

As described herein, the analysis tool 130 is configured to analyze the video data (received from the recording device 105) to determine a detected state of the user that is currently exercising. The detected state may include at least one from the group consisting of: facial expression (e.g., tired, bored, calm, level of exertion, level of pain); perspiration detection; breathing interval estimation; and skin tone change.

The detected state may be facial expression, in which case the analysis tool 130 may apply image processing techniques to the video data, in particular facial recognition programming and/or facial analysis programming, to determine whether the user is tired, bored, calm, experiencing a certain level of exertion, or experiencing a certain level of pain while exercising. For example, the analysis tool 130 may use facial recognition/analysis techniques to compare the user's facial expression (captured in the video data) to a database of categorized facial expressions to determine that the user's facial expression most closely matches a category of facial expression, e.g., tired, bored, calm, low exertion, medium exertion, high exertion, no pain, low pain, medium pain, high pain. Specifically, the analysis tool 130 may use deep learning or action unit (AU) detection in conjunction with the database of categorized facial expressions to determine a category of the user's facial expression. Aspects of the invention are not limited to these exemplary facial expressions, and other facial expressions may be used in implementations. In this manner, the analysis tool 130 may be configured to determine, in real time, a category of facial expression of the user while the user is exercising.

The detected state may be perspiration detection, in which case the analysis tool 130 may apply image processing techniques to the video data to determine whether the user is perspiring while exercising. For example, the analysis tool 130 may use image processing techniques to compare an image of the skin texture of the user (captured in the video data) to a database of categorized images of skin textures that correspond to one of a perspiring state and a non-perspiring state. In this manner, the analysis tool 130 may be configured to determine, in real time, whether or not the user is perspiring while exercising.

The detected state may be breathing interval estimation, in which case the analysis tool 130 may apply image processing techniques to the video data to determine a breathing interval of the user while exercising. For example, the analysis tool 130 may use image processing techniques to track the changing shape of the user's mouth and nose to determine when the user is inhaling and exhaling, e.g., by comparing images of the user's mouth and nose to a database of categorized images of mouth and nose that correspond to one of an inhaling state and an exhaling state. Additionally, by analyzing times associated with the video images of the user's mouth and nose, the analysis tool 130 may determine an amount of time that elapses between each determined inhale and exhale of the user. In this manner, the analysis tool 130 may be configured to determine, in real time, a breathing interval (e.g., number of breaths per minute) of the user while exercising.

The detected state may be skin tone change, in which case the analysis tool 130 may apply image processing techniques to the video data to determine that the user's skin tone has changed from a first tone to a second tone user while exercising. A change in skin tone may indicate, for example, that the user's skin is flush due to physical exertion. For example, the analysis tool 130 may use image processing techniques to observe the user's initial skin tone at an early stage of the exercising and detect if the user's skin tone changes from the initial skin tone to a different skin tone at a later stage of the exercising. In this manner, the analysis tool 130 may be configured to determine, in real time, a skin tone change of the user while exercising.

Still referring to FIG. 2, in embodiments, the analysis server 110 is configured to provide feedback to the user based on the detected state of the user (as determined by the analysis tool 130). The feedback may be based solely on the detected state of the user, or may be based on comparing the detected state of the user to user data (e.g., data associated with the particular user). The feedback may include at least one from the group consisting of: displaying an indication of the detected state; displaying an indication of user data; displaying a recommendation; and automatically adjusting an element of the user's environment. The feedback, when comprising a display of information, may be provided via the notification device 115, which may comprise a video display device (e.g., an LCD screen of a television, computer, smartphone, etc.).

In an embodiment, the feedback may be based solely on the detected state of the user, e.g., without comparing the detected state to the user data. In this embodiment, the server 110 may transmit signals to the notification device 115 to cause the notification device 115 to display an indication 140 of the user's detected state (or plural detected states) in real time. In this manner, the user is provided with information that they may employ in deciding how to continue (or modify) their exercise.

For example, the server 110 may display an indication of the user's detected facial expression on the notification device 115, and change the displayed indication in real time as changes in the user's facial expression are detected by the server 110. As another example, the server 110 may display an indication of the user's detected perspiration state on the notification device 115, and change the displayed indication in real time as changes in the user's perspiration state are detected by the server 110. As another example, the server 110 may display an indication of the user's detected breathing interval (e.g., breathing rate) on the notification device 115, and change the displayed indication in real time as changes in the user's breathing interval are detected by the server 110. As another example, the server 110 may display an indication of the user's detected skin tone on the notification device 115, and change the displayed indication in real time as changes in the user's skin tone are detected by the server 110. The server 110 may be configured to simultaneously display plural indications of different detected states on the notification device 115, e.g., display detected facial expression, perspiration state, breathing interval, and skin tone all at the same time on the notification device 115.

In another embodiment, the feedback may be based on comparing the detected state of the user to user data (e.g., data associated with the particular user). The user data may comprise, for example, at least one of: age, weight, height, gender, health conditions, and prescribed training. The user data may be defined by data that is input via the input device 120, which may be a computer device that permits a user to enter data via any suitable method such as touch screen, keyboard, button(s), dial(s), and file transfer.

Prescribed training may be defined by the user, a medical professional (e.g., a doctor), or an exercise professional (e.g., trainer, coach, etc.). Prescribed training may define one or more thresholds for the user in terms of possible detected states (e.g., tired, bored, calm, low exertion, medium exertion, high exertion, no pain, low pain, medium pain, high pain, perspiration, breathing interval, and skin tone change). Prescribed training may be defined in terms of rules regarding one or more detected states that the user is recommended to achieve during exercising. For example, an exemplary prescribed training rule may define that a user is recommended to exhibit: medium or high exertion, perspiration, and a breathing interval of at least thirty breaths per minute. Prescribed training may also be defined in terms of rules regarding one or more detected states that the user is recommended to avoid during exercising. For example, an exemplary prescribed training rule may define that a user is recommended to not exhibit: high pain or a breathing interval exceeding fifty breaths per minute. These examples are not intended to be limiting, and any desired configuration of states may be defined in one or more prescribed training rules. Moreover, a single user may have plural different prescribed training rules that are simultaneously applied by the analysis tool 130.

In embodiments, user data that is entered via the input device 120 is transmitted to the server 110 and used by the analysis tool 130 only during a single exercise session. In such an embodiment, the server 110 does not store the user data for use in subsequent exercise sessions.

In other embodiments, user data that is input via the input device 120 is transmitted to the server 110 and stored in association with an identity of the user that provided the data. In this manner, the user data may be entered one time and then retrieved from storage during future exercise sessions by the same user. For example, a user may login via the input device 120, and the server 110 may retrieve the user data based on the user identity determined from the user login. In another embodiment, alternatively to a user logging in via the input device 120, the server 110 may automatically determine an identity of a user based on image analysis (e.g., facial recognition) of a video of the face of the user obtained via the recording device 105. In this manner, the server 110 may automatically determine the identity of the user and obtain the user data based on the determined user identity.

Still referring to the embodiment in which the feedback is based on comparing the detected state to the user data, the feedback may include a visual indication 140 of the detected state and a visual indication 145 of a portion of the user data, such as a prescribed training rule, without a recommendation (e.g., displaying the detected state and a related prescribed training rule simultaneously on the notification device 115). In this manner, the user may use the feedback to make their own determination as how whether and how to adjust their level of exertion (e.g., stay the same, slow down, or speed up).

The feedback may optionally include a recommendation to the user based on the comparison of the detected state and the user data. For example, the server 110 may display a recommendation 150 to the user (e.g., "slow down" or "change the exercise" or "increase recovery time") when a detected state exceeds a recommended state as defined in a prescribed training rule (e.g., a detected level of exertion/pain/breathing interval exceeds a maximum level of exertion/pain/breathing interval defined in a prescribed training rule). Similarly, the server 110 may display a recommendation to the user (e.g., "speed up" or "increase effort" or "decrease recovery time") when a detected state is lower than a recommended state as defined in a prescribed training rule (e.g., a detected level of exertion is less than a minimum level of exertion defined in a prescribed training rule). In this embodiment, the server 110 may simultaneously display the visual indication 140 of the detected state and the visual indication 145 of the prescribed training along with the recommendation 150.

In further embodiments, the server 110 may automatically control an element of the user's environment based on the comparison of the detected state and the prescribed training. The element may comprise the equipment 128 and/or a climate control system 155 in the room where the equipment 128 is located. For example, when a detected level of exertion is greater than a prescribed level of exertion (e.g., as defined in a prescribed training rule), the server 110 may automatically perform one of: decrease the resistance of a weight machine; decrease the speed and/or incline of a treadmill; decrease the resistance of a stationary bicycle elliptical machine, or rowing machine; and decrease a temperature of the room in which the user is located. Conversely, when a detected level of exertion is less than a prescribed level of exertion (e.g., as defined in a prescribed training rule), the server 110 may automatically perform one of: increase the resistance of a weight machine; increase the speed and/or incline of a treadmill; increase the resistance of a stationary bicycle, elliptical machine, or rowing machine; and increase a temperature of the room in which the user is located. For example, the server 110 may be operatively connected to a controller and/or actuator on the equipment 128 to send control signals to the equipment 128 to automatically adjust the resistance, speed, and/or incline of the exercise machine. Similarly, the server 110 may be operatively connected to a thermostat of a climate control system 155 of the room in which the user is located to send control signals to the thermostat to automatically adjust the temperature of the room.

Aspects of the invention are not limited to the aforementioned examples of feedback, and other actions may be automatically performed based on the comparison of the detected state and the user data. For example, the server 110 may provide a recommendation via the notification device 115 recommending that the user ingest liquid or change the room temperature based on the server 110 detecting that the user's perspiration level is too high, e.g., has detected a state of perspiration for a predefined amount of time. As another example, the server 110 may provide a recommendation via the notification device 115 recommending that the user adjust their breathing behavior based on the server 110 detecting that the user's breathing intervals are too short or too long during an exercise. In yet another example, the server 110 may provide a recommendation via the notification device 115 based on comparing the detected state of the user to health data of the user, e.g., by determining very low blood glucose levels based on detecting tremors, dizziness, pallor, excessive cold sweat, and weakness.

In embodiments, the recording device 105, the notification device 115, and the input device 120 may be combined into a single device, such as a computer system 160 (e.g., similar to computer system 12 of FIG. 1) that comprises an integrated video camera for recording video images, a display screen for displaying visual output, and an input system for receiving user input. In an exemplary implementation, the computer system 160 is physically connected to the equipment 128 (e.g., a treadmill, stationary bicycle, rowing machine, weight machine, etc.). In another exemplary implementation, the computer system 160 is physically connected to a wall, ceiling, or floor in the vicinity of the equipment 128. Alternatively to being combined in a single system, each of the recording device 105, the notification device 115, and the input device 120 may be separate devices. Each respective one of the devices may be physically connected to the equipment 128 or physically connected to a wall, ceiling, or floor in the vicinity of the equipment 128.

In embodiments, the server 110 is operatively connected to a sensor 165, which may comprise one or more of: a heart rate sensor; a skin temperature sensor; a sleep quality sensor; an oxygen saturation sensor; and a galvanic skin response sensor. In this manner, the server 110 determines a detected state of the user based on a combination of the video data from the recording device 105 and the data from the sensor 165.

Figure 3:
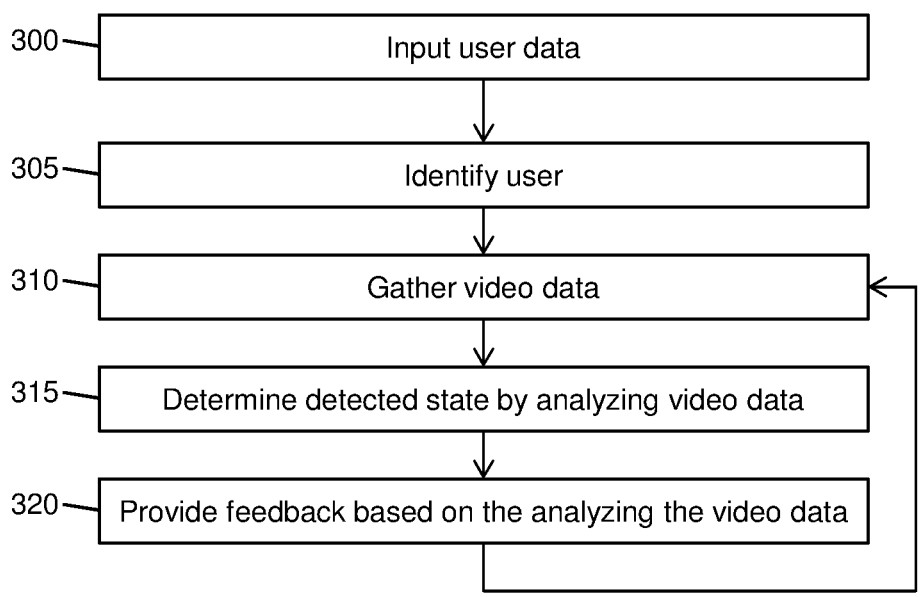
FIG. 3 shows a flowchart of a method in accordance with aspects of the invention.

FIG. 3 depicts a method of adapting physical activities and exercises based on facial analysis by image processing in accordance with aspects of the invention. The steps of the method may be performed in the system of FIG. 2 and are described with reference to the elements described in FIG. 2.

Referring to FIG. 3, at step 300 the system 100 receives an input of user data. Step 300 may be performed in the manner described with respect to FIG. 2, e.g., by a user, a medical professional, or an exercise professional providing input to the input device 120. The user data may include, for example, at least one of: age, weight, height, gender, health conditions, and prescribed training.

At step 305, the system 100 identifies the user. In embodiments, the user provides login information via the input device 120 and the server 110 determines the user identity based on the login information, e.g., as described with respect to FIG. 2. In other embodiments, the server 110 automatically determines the user identity based on image analysis of a video of the face of the user obtained via the recording device 105, e.g., as described with respect to FIG. 2.

At step 310, the system 100 gathers video data of the user's face (e.g., facial data) while the user is exercising. Step 310 may be performed in the manner described with respect to FIG. 2, e.g., by the recording device 105 obtaining video data of the user and transmitting the video data to the server 110 via the network 125.

At step 315, the system 100 determines a detected state of the user based on analyzing the video data (e.g., facial data) from step 310. Step 315 may include analyzing the video data using facial analysis to determine a state of the user based on facial data of the user. Step 315 may be performed in the manner described with respect to FIG. 2, e.g., by the server 110 analyzing the video data to determine at least one of: tired, bored, calm, low exertion, medium exertion, high exertion, no pain, low pain, medium pain, high pain, perspiration, breathing interval, and skin tone change. Other states may detected by the server 110 using additional image processing rules programmed in the analysis tool 130 of the server 110. In a preferred embodiment, the analyzing includes facial analysis image processing to determine a facial expression of the user, and may additional include image processing to detect at least one of perspiration, breathing interval, and skin tone change.

At step 320, the system 100 provides feedback to the user based on the analyzing the video data from step 315. Step 320 may be performed in the manner described with respect to FIG. 2, e.g., by the notification device 115 displaying at least one of an indication of the detected state, user data, and a recommendation. In an embodiment, the feedback is not based on a comparison of the detected state to the user data, and the feedback in this embodiment is the notification device 115 displaying an indication of the detected state in real time (based on data received from the server 110). In another embodiment, the feedback is based on a comparison of the detected state to the user data, and the feedback in this embodiment is the notification device 115 displaying at least one of an indication of the detected state in real time, user data, and a recommendation. The user data that may be displayed at step 320 may include, for example, a prescribed training rule that is related to the detected state that is currently being displayed. The recommendation that may be displayed at step 320 may include, for example, a recommendation to adjust the user's exercise based on comparing the detected state to the prescribed training rule.

The feedback at step 320 may optionally include the system 100 automatically adjusting an element of the user's environment. For example, as described with respect to FIG. 2, the server 110 may send control signals to at least one of the equipment 128 and a climate control unit 155 to automatically adjust an element of the user's environment based on the analyzing the video data from step 315.

In embodiments, a service provider, such as a Solution Integrator, could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
    identifying, by a computer device, a user;
    receiving, by the computer device, video data of a face region of the user while the user is engaged in exercise or physical activity;
    analyzing, by the computer device, the video data to determine a detected state of the user and to determine a change in a skin tone of the user, wherein the analyzing the video data comprises performing facial analysis using the video data to determine a level of exertion of the user and to determine a detected breathing interval of the user by tracking a changing shape of the user's mouth and nose; and
    providing, by the computer device, feedback to the user based on the analyzing the video data,
    wherein the providing the feedback comprises the computer device causing a notification device to display an indication of the detected state, and
    wherein the indication of the detected state includes simultaneously displaying on the notification device a detected facial expression and a detected perspiration state.

2. The method of claim 1, wherein the identifying the user comprises:
    the computer device receiving login data from the user via an input device; and
    the computer device determining an identity of the user based on the login data.

3. The method of claim 1, wherein the identifying the user comprises the computer device determining an identity of the user by performing facial recognition using the video data.

4. The method of claim 1, wherein the video data is received by the computer device via network communication from a recording device recording the video data.

5. The method of claim 1, wherein:
the computer device receives the video data from a video camera connected to exercise equipment on which the user is exercising;
the computer device determines, based on comparing the detected state to a prescribed training rule, that the level of exertion is less than a prescribed level of exertion; and
the providing the feedback comprises the computer device controlling the exercise equipment to increase a resistance, speed, or incline of the exercise equipment.

6. The method of claim 1, wherein:
the computer device receives the video data from a video camera connected to exercise equipment on which the user is exercising;
the computer device determines, based on comparing the detected state to a prescribed training rule, that the level of exertion is more than a prescribed level of exertion; and
the providing the feedback comprises the computer device controlling the exercise equipment to decrease a resistance, speed, or incline of the exercise equipment.

7. The method of claim 1, wherein the providing the feedback comprises the computer device causing the notification device to display an indication of a prescribed training rule.

8. The method of claim 7, wherein the providing the feedback comprises the computer device causing the notification device to display a recommendation that is based on a comparison of the detected state to a prescribed training rule.

9. The method of claim 1, wherein the providing the feedback comprises the computer device causing the notification device to display the indication of the detected state in real time while the user is engaged in the exercise or the physical activity.

10. The method of claim 1, wherein the providing the feedback comprises the computer device controlling equipment on which the user is engaged in the exercise or the physical activity.

11. The method of claim 1, wherein the providing the feedback comprises the computer device adjusting a temperature of a room in which the user is engaged in the exercise or the physical activity.

12. The method of claim 1, wherein the analyzing the video data is to determine a level of pain of the user.

13. A system, comprising:
a CPU, a computer readable memory and a computer readable storage medium associated with a computing device;
program instructions to receive video data of a face region of the user while the user is engaged in exercise on exercise equipment;
program instructions to determine a detected state of the user, wherein the determining the detected state includes: analyzing the video data to determine a detected facial expression of the user; and analyzing the video data to determine a detected breathing interval of the user by tracking a changing shape of the user's mouth and nose; and
program instructions to provide feedback to the user based on comparing the detected state to a prescribed training rule,
wherein the computing device comprises a server that receives the video data from a recording device via a network,
wherein the providing the feedback comprises the server transmitting data to a notification device via the network,
wherein the providing the feedback further comprises the server causing the notification device to display a recommendation based on comparing the detected state to the prescribed training rule,
wherein the indication of the detected state includes simultaneously displaying on the notification device the detected facial expression and the detected breathing interval, and
wherein the program instructions are stored on the computer readable storage medium for execution by the CPU via the computer readable memory.

14. The system of claim 13, wherein the providing the feedback comprises the server causing the notification device to display the indication of the detected state in real time while the user is engaged in the exercise on the exercise equipment.

15. The system of claim 13, wherein the providing the feedback comprises the server controlling the exercise equipment to adjust a resistance, speed, or incline of the exercise equipment.

16. The system of claim 13, wherein the providing the feedback comprises the computer device adjusting a temperature of a room in which the user is engaged in the exercise on the exercise equipment.

17. The system of claim 13, wherein the tracking a changing shape of the user's mouth and nose comprises comparing images of the user's mouth and nose to a database of categorized images of mouths and noses that correspond to an exhaling state.

18. A computer program product comprising a computer readable storage medium having program instructions embodied therewith, the program instructions executable by a computing device to cause the computing device to:
receive video data of a face region of the user while the user is engaged in exercise or physical activity on exercise equipment comprising one of a treadmill, stationary bicycle, rowing machine, and weight machine;
determine a detected state of the user, wherein the determining the detected state includes: analyzing the video data to determine when the user is inhaling and exhaling and to determine a perspiration state of the user and a change in a skin tone of the user and to determine a detected breathing interval of the user by tracking a changing shape of the user's mouth and nose; and
provide feedback to the user based on the analyzing the video,
wherein the providing the feedback comprises the server causing the notification device to concurrently display: an indication of the detected state; an indication of a prescribed training rule; and a recommendation based on comparing the detected state to the prescribed training rule,
wherein the indication of the detected state includes simultaneously displaying on the notification device the detected perspiration state and the detected skin tone.

19. The computer program product of claim 18, wherein the providing the feedback comprises the server sending a signal to control equipment on which the user is engaged in the exercise or the physical activity.

20. The computer program product of claim 18, wherein the providing the feedback comprises the server sending a signal to adjust a temperature of a room in which the user is engaged in the exercise or physical activity on the exercise equipment.

* * * * *